(12) United States Patent
Orol et al.

(10) Patent No.: US 11,229,744 B2
(45) Date of Patent: Jan. 25, 2022

(54) AUTO-INJECTION DEVICE

(71) Applicant: BDRtech LLC, Phoenix, AZ (US)

(72) Inventors: Daniel Harris Orol, Raleigh, NC (US); Benjamin Victor Bernstein, Rosemont, PA (US); Reed Evan Ginsberg, Jericho, NY (US); Spencer Quinn Fox, Cochranville, PA (US); Jacob Edward Snipes, Meadowbrook, PA (US); Alexander McIver Garcia, Brooklyn, NY (US)

(73) Assignee: BDRtech, LLC, Phoenix, AZ (US)

( * ) Notice: Subject to any disclaimer, the term of this patent is extended or adjusted under 35 U.S.C. 154(b) by 0 days.

(21) Appl. No.: 17/090,236

(22) Filed: Nov. 5, 2020

(65) Prior Publication Data
US 2021/0052812 A1 Feb. 25, 2021

Related U.S. Application Data

(63) Continuation of application No. 16/607,323, filed as application No. PCT/US2019/023417 on Mar. 21, 2019, now abandoned.
(Continued)

(51) Int. Cl.
*A61M 5/20* (2006.01)
*A61M 5/00* (2006.01)
*A61M 5/32* (2006.01)

(52) U.S. Cl.
CPC .......... *A61M 5/2033* (2013.01); *A61M 5/002* (2013.01); *A61M 5/3202* (2013.01);
(Continued)

(58) Field of Classification Search
CPC .............. A61M 5/2033; A61M 5/3202; A61M 5/14244; A61M 5/326; A61M 5/3273;
(Continued)

(56) References Cited

U.S. PATENT DOCUMENTS

2005/0171477 A1* 8/2005 Rubin ................. A61M 5/2033
604/156
2008/0289984 A1* 11/2008 Raven ................ B65D 47/0814
206/364
(Continued)

FOREIGN PATENT DOCUMENTS

WO WO-2004060445 A2 * 7/2004 .......... A61M 5/3257

*Primary Examiner* — Emily L Schmidt
*Assistant Examiner* — Leah J Swanson
(74) *Attorney, Agent, or Firm* — NK Patent Law

(57) ABSTRACT

The present application discloses a device that is designed to inject into a user medicinal or non-medical substance upon activation. The device is light and compact, suitable for wearing or carrying by a user. The device comprises a needle, a syringe, and two sets of springs. The syringe comprises a plunger and a chamber for storing an injection substance. The needle is configured to be coaxial and in communication with the syringe. Each set of springs may comprise one or more springs. The first set of springs is configured to push the needle and the second set of springs is configured to move the plunger. In one exemplary embodiment, the device is enclosed in a sealed case and the device may be made to resemble a watch.

15 Claims, 18 Drawing Sheets

Related U.S. Application Data

(60) Provisional application No. 62/646,518, filed on Mar. 22, 2018.

(52) U.S. Cl.
CPC . *A61M 2005/2026* (2013.01); *A61M 2209/06* (2013.01); *A61M 2209/088* (2013.01)

(58) Field of Classification Search
CPC .............. A61M 5/3275; A61M 5/3287; A61M 2005/14272; A61M 2005/2013; A61M 2005/1586; A61M 2005/3261; A61M 2005/3263; A61M 2005/3264; A61M 2005/3267; A61M 2005/3268; A61M 2005/2073; A61M 2005/208; A61M 2005/14268; A61M 2005/14264; A61M 2005/2026

See application file for complete search history.

(56) References Cited

U.S. PATENT DOCUMENTS

| | | | |
|---|---|---|---|
| 2014/0046259 A1* | 2/2014 | Reber | .................. A61M 5/2033 604/136 |
| 2019/0105442 A1* | 4/2019 | Kapas | ................... A61M 5/002 |

* cited by examiner

AUTO-INJECTION DEVICE

RELATED APPLICATIONS

This application is a continuation of U.S. patent application Ser. No. 16/607,323, titled "AUTO-INJECTION DEVICE" and filed on Oct. 22, 2019, which is a 371 National Phase of PCT Application No. PCT/US2019/023417, titled "AUTO-INJECTION DEVICE" and filed on Mar. 21, 2019, which claims priority to U.S. Provisional Application No. 62/646,518, titled "Wearable Medical Drug Auto-Injector" and filed on Mar. 22, 2018, the entire contents of which is incorporated herein in its entirety.

FIELD OF TECHNOLOGY

The present disclosure relates generally to medical devices, and more specifically to a light and compact auto-injection device suitable for wearing or carrying.

BACKGROUND

Anaphylaxis is a life-threatening medical condition that affects millions of people across all ages. When an individual with this condition contacts or ingests an allergen they are sensitive to, such as nuts, insect venom, shellfish, etc., the individual's throat begins to swell and breathing becomes difficult. If the individual does not receive an adequate dose of proper medication administered in a prescribed way within a preferred time limit, the condition can be fatal. In the case of anaphylaxis, the procedure recommended by doctors is to administer epinephrine intramuscularly into the thigh within a few minutes of the onset of the medical condition.

Anaphylaxis patients are encouraged to carry an epinephrine auto-injection device, e.g. EpiPen, that contains an effective dose of epinephrine and is ready for use by patients themselves. The auto-injection device can be activated by a stabbing motion at the injection site. After activation, the drug is automatically administered. Patients with other potentially life-threatening conditions, e.g., hyperglycemia, can also benefit from carrying or wearing an auto-injection device for emergency use.

Prior art auto-injection devices are bulky and heavy. They are not convenient to be carried around. Nor can they be worn by users as a wearable device. The present application discloses an auto-injection device that is light and compact, suitable for wearing or carrying by users in their daily activities.

SUMMARY

Accordingly, it is an objective of the present disclosure to teach an auto-injection device that is light and compact and can be carried as a wearable device.

In some embodiments, an exemplary auto-injection device comprises a syringe, a needle, and two sets of springs. The syringe comprises a plunger and a chamber for storing an injection substance. The needle is connected to and in communication with the syringe. In one embodiment, the needle and the syringe are coaxial. Each set of springs comprises one or more springs. The first set of springs is coupled to the syringe and configured to push the needle. The second set of springs is coupled to the plunger and configured to push the plunger. The auto-injection device may be housed in a casing. In one embodiment, the casing is sealed to prevent contamination. In another embodiment, the needle may be protected by a protective cover to prevent contamination.

In some embodiments, each set of springs comprises a compressed state and a released state. The first set of springs is configured to move the needle outside of the casing when the first set of springs is in the released state. When the first set of springs is released, the second set of springs is released from its compressed state and drives the plunger to inject the substance stored in the chamber into the patient. In some embodiments, the first and second set of springs are released in sequence. The second set of springs is released after the first set of springs is released. In some embodiments, the first and second sets of springs may be released substantially simultaneously.

In some embodiments, the auto-injection device comprises a first activator configured to release the first set of springs. In one embodiment, the syringe of the auto-injection device is configured to compress the first set of springs when resting on one or more cantilevers. The first activator is configured to bend or push the cantilevers and move the syringe off the cantilevers in order to release the first set of springs. Once released from the compressed state, the first set of springs pushes the needle outside the casing.

In some embodiments, the auto-injection comprises a second activator configured to release the second set of springs. When the second set of springs is released from the compressed state, the second set of springs drives the plunger of the syringe to inject the substance stored in the chamber. In one embodiment, the second activator comprises a tube and a pin. The tube is configured with one or more cross-holes in the wall. The pin is inside the tube and is configured to move from an inserted position to a pulled-up position. One or more identical balls are held inside the cross-holes. The size of the balls is larger than the thickness of the wall of the tube. When the pin is in the inserted position, the balls are pushed by the pin to extrude outside the outer-wall of the tube and act as a stopper to hold the second set of springs in the compressed state. When the pin is in the pulled-up position, the one or more balls are configured to move towards the interior of the tube to release the second set of the springs. The released springs in the second set push the plunger to inject a stored substance.

In some embodiments, the auto-injection device comprises a revolving sheath that blocks the needle after injection. The sheath is configured to move from a closed position to an open position. When in the closed position, the revolving sheath rests on the casing. When in the open position, the revolving sheath blocks the needle. In one embodiment, the revolving sheath is attached to the casing via a revolving peg.

In some embodiments, a wearable device comprising a watch-sized case and an auto-injection cartridge is disclosed. The case comprises a frame, a cover and one or more outer-covers. The frame comprises two cantilevers attached to two opposing interior sides of the frame respectively. The auto-injection cartridge is inset onto the cantilevers. When the auto-injection cartridge slides off the cantilevers, the wearable device is activated. In one embodiment of the wearable device, a revolving sheath is attached to the cover to block the needle of the auto-injection cartridge after use.

In some embodiments, a wearable device comprising a telescoping case and an auto-injection device is disclosed. The telescoping case changes shape by extension using a telescoping mechanism. In this embodiment, the case comprises two or more separate components that together enclose the auto-injection device. Attached to the rear section of the device are small snap-fit pieces that move parallel to the body of the device within a confined space. The confined space compresses the snap-fit pieces such that they are in a compressed state before being activated. When the snap-fit pieces exit the confined space, they are allowed to expand. In the expanded state, the snap-fit pieces cannot return to the confined space, so the rear section cannot be pushed back towards the needle tip. After the body of the device has expanded, the set of activation springs remain in a partially compressed state. This ensures that they can push the needle out of the device upon activation.

BRIEF DESCRIPTION OF THE DRAWINGS

These and other features of the present disclosure will become readily apparent upon further review of the following specification and drawings. In the drawings, like reference numerals designate like parts having similar functionality throughout the views. Like parts may be designed differently in different embodiments. Components in the drawings are not necessarily drawn to scale, the emphasis instead being placed upon clearly illustrating the principles of the present disclosure.

DETAILED DESCRIPTION

Embodiments of the disclosure are described more fully hereinafter with reference to the accompanying drawings, in which preferred embodiments of the disclosure are shown. The various embodiments of the disclosure may, however, be embodied in many different forms and should not be construed as limited to the embodiments set forth herein. Rather, these embodiments are provided so that this disclosure will be thorough and complete, and will fully convey the scope of the disclosure to those skilled in the art.

Figure 1:
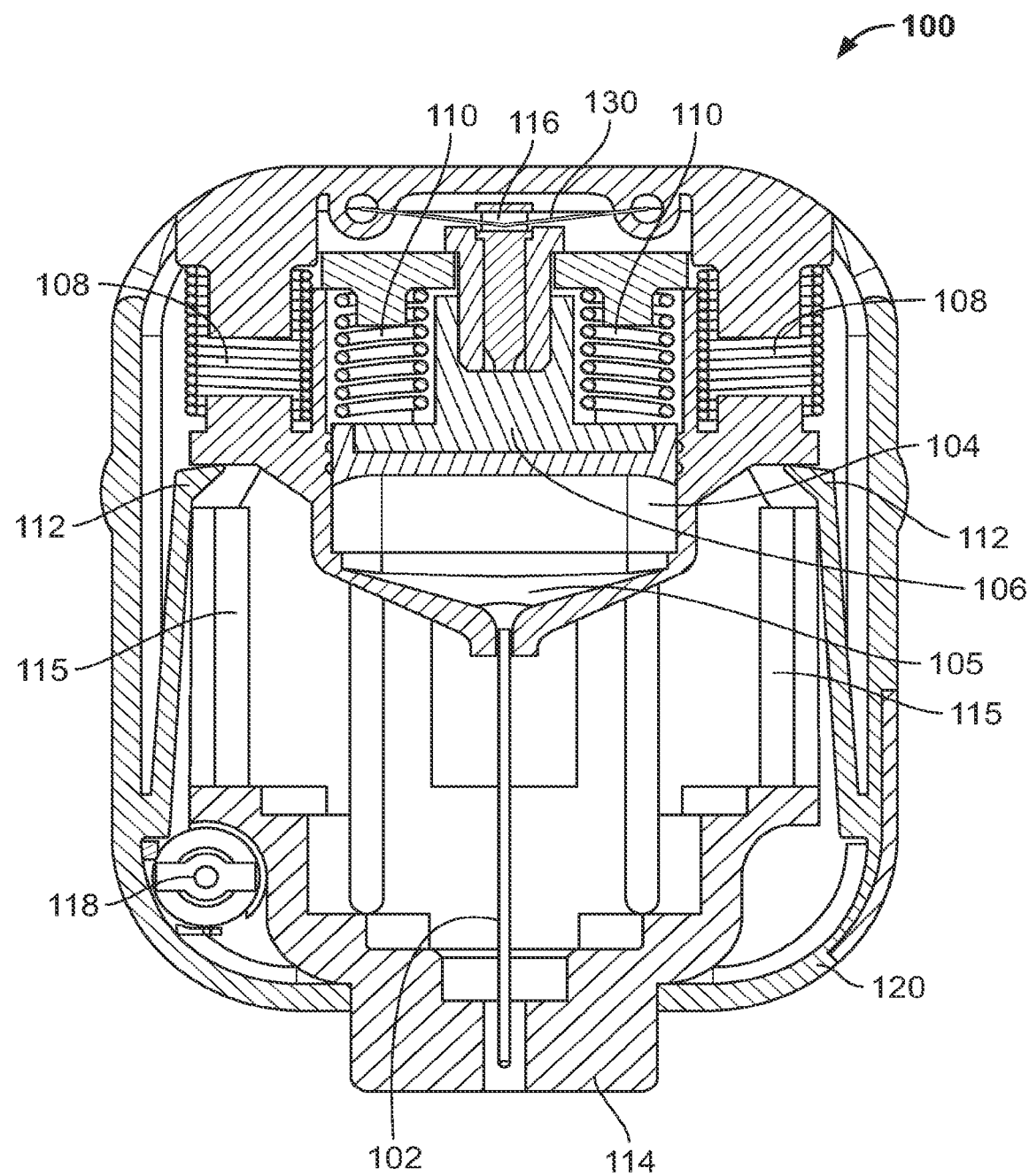
FIG. 1 is a cross-section view of a first embodiment of an exemplary auto-injection device taught by the present disclosure.

In referring to FIG. 1, an auto-injection device 100 is depicted as comprising a needle 102, a syringe 104, a first set of springs 108 and a second set of springs 110. The needle 102 is connected to the syringe 104 and in communication with the syringe 104. In some embodiments, the needle 102 and the syringe 104 are coaxial. The syringe 104 comprises a plunger 106 and a chamber 105 for storing an injection substance. The first set of springs 108 is coupled to the syringe 104 and configured to push the needle 102. The second set of springs 110 is coupled to the plunger 106 and configured to push the plunger 106.

In the embodiment shown in FIG. 1, the first set of springs 108 and the second set of springs 110 each comprise two springs. In other embodiments, each of the first and second set of springs 108 and 110 may comprise one or more springs. For example, in the embodiments shown in FIG. 13 and FIG. 14, each set comprises one spring. (More detailed description of FIGS. 13 and 14 can be found in later sections.)

In referring to FIG. 1, the auto-injection device 100 is housed in a casing 120. The casing 120 comprises one or more cantilevers 112 for supporting the syringe 104 or pushing the syringe 104 against the first set of springs 108 when the springs are in a compressed state. Each of the first and second set of springs 108 and 110 comprises a compressed state and a released state. In FIG. 1, both sets of springs are in a compressed state. Two activators 114 and 116 are configured to release the two sets of springs respectively. (The auto-injection device 100 further comprises a revolving peg 118, the functionality of which will be explained in detail in FIGS. 10a and 10b.)

The first activator 114 (also see FIG. 4) is configured to release the first set of springs 108 from the compressed state. When the first activator 114 is pushed inwards, i.e., towards the casing 120, the straight bars 115 press the cantilevers 112 outward. The cantilevers 112 are pushed farther apart and the distance between the two cantilevers 112 increases.

Figure 2:
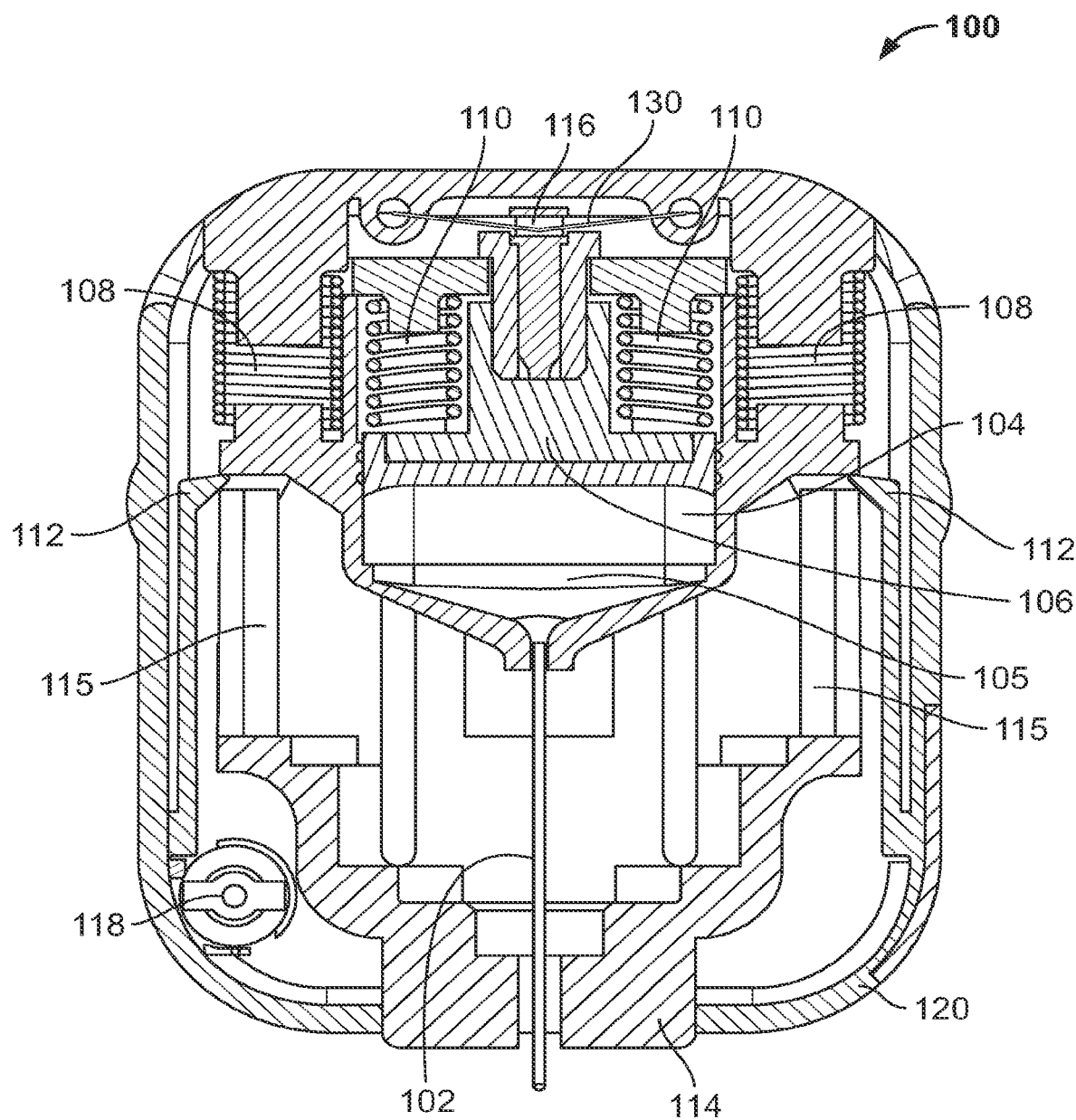
FIG. 2 illustrates the exemplary auto-injection device in an activated state.

FIG. 2 depicts a state of the first activator 114 during the activation process. The cantilevers 112 are bent towards the casing 120 under the pressure of the straight bars 115. In FIG. 2, the needle 102 is thrust outside of the casing 120 but the syringe 104 has not fallen off the cantilevers 112 yet. As the activator 114 continues to push upwards, the distance between the two cantilevers 112 increases until it is wider than the width of the syringe 104 and the syringe 104 moves off the cantilevers 112. The first set of springs 108 is released and pushes the syringe 104 downward to thrust the needle 102 out of the casing 120 and into the injection site.

As the syringe 104 moves downward, the second activator 116 (see also FIGS. 5a and 5b) is activated to release the second set of springs 110 from a compressed state to a released state. The second set of springs 110 is coupled to the plunger 106 of the syringe 104. As the second set of springs 110 is released, the springs push the plunger 106 down. The chamber 105 underneath the plunger 106 stores the substance to be injected, e.g., epinephrine. As the plunger 106 moves downward, the substance is pushed into the needle 102, which is in communication with the syringe 104. Through the needle 102, the substance is injected into a person. See FIG. 3.

Figure 4:
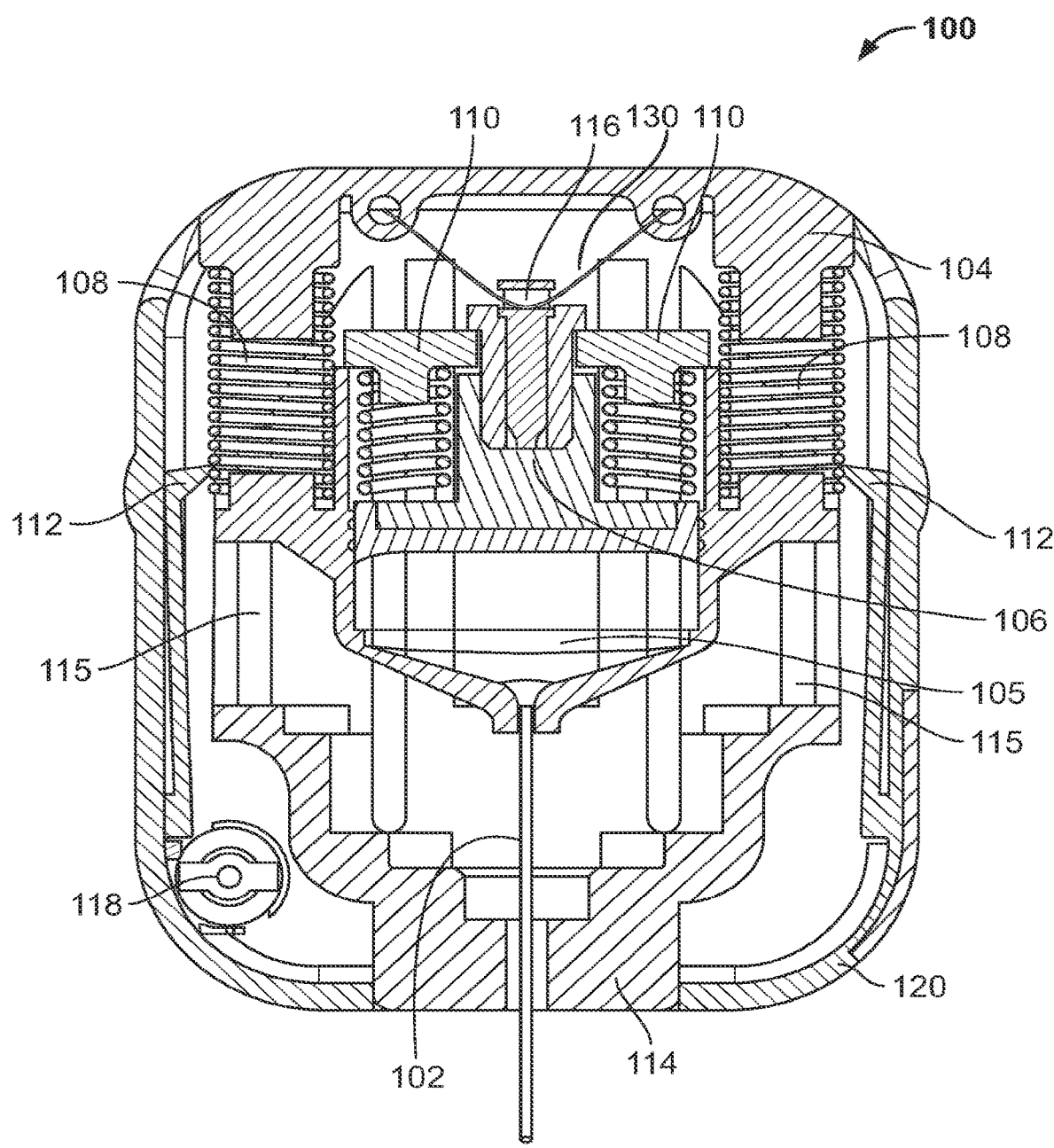
FIG. 4 illustrates an exemplary embodiment of the first activator.

FIG. 4 illustrates one exemplary embodiment in which the first activator 114 and the second activator 116 are activated in sequence. In FIG. 4, the first activator 114 is shown to have been fully activated. The first activator 114 is pressed inside the casing 120. The syringe 104 has moved off the cantilevers 112 and the first set of springs 108 has pushed the needle 102 partially outside of the casing 120. The second activator 116 however has not been activated and the second set of springs 110 is still in a compressed state.

Figure 3:
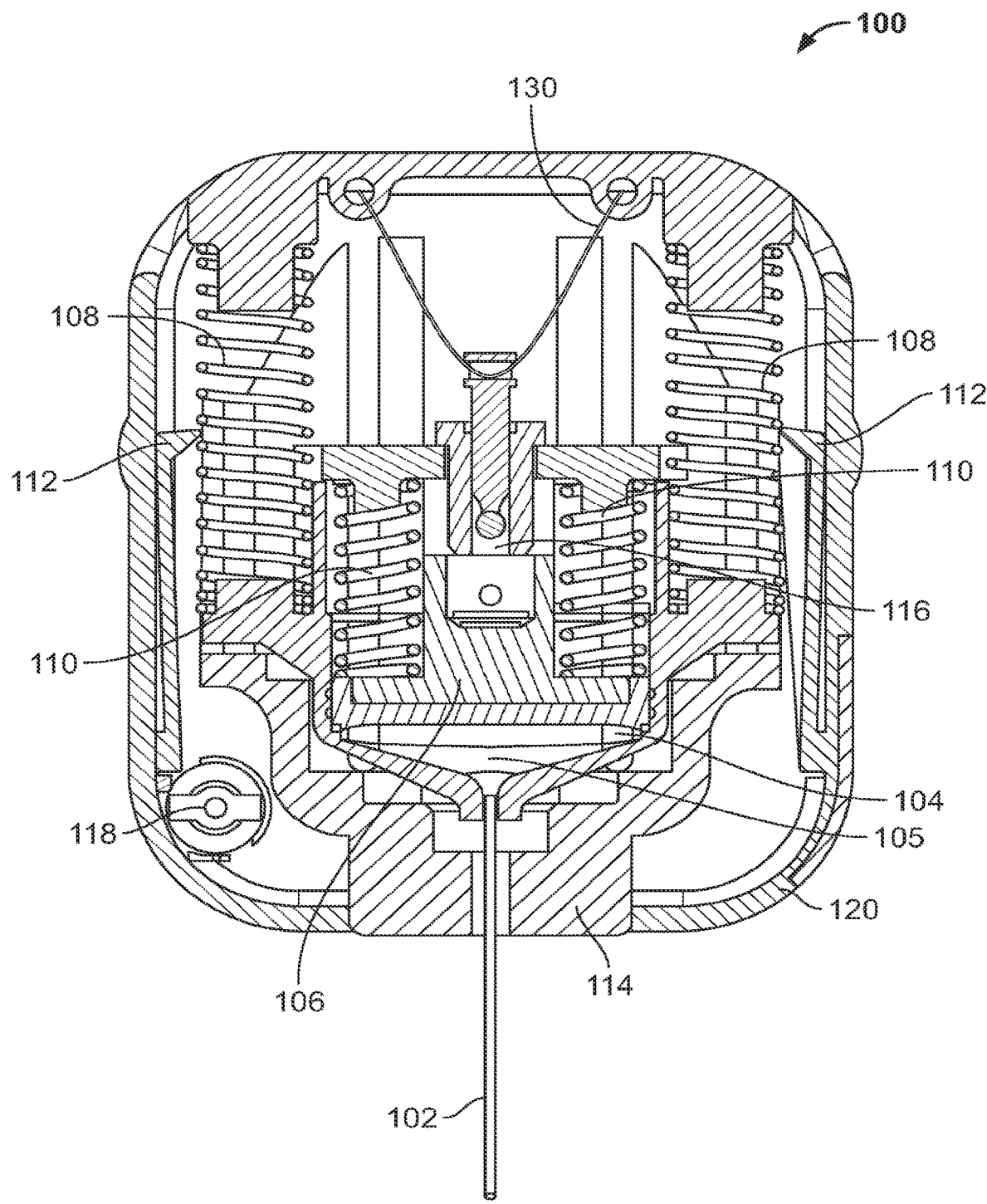
FIG. 3 illustrates the exemplary auto-injection device after injection.
Figure 5A:
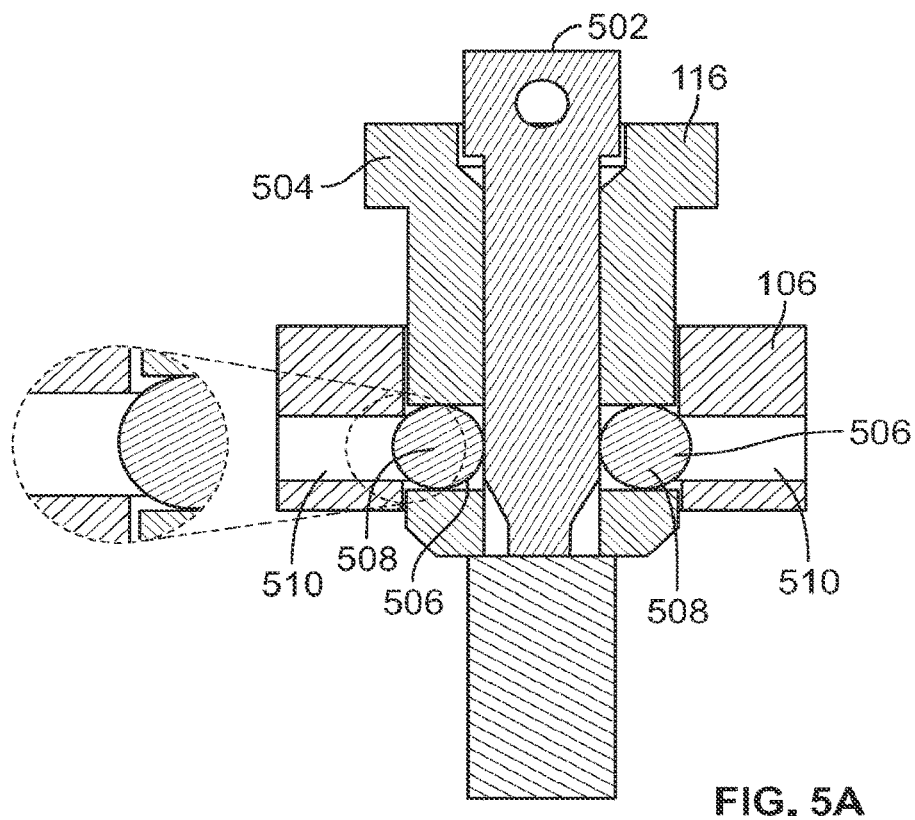
FIGS. 5a-5c illustrate an exemplary embodiment of the second activator.
Figure 5B:
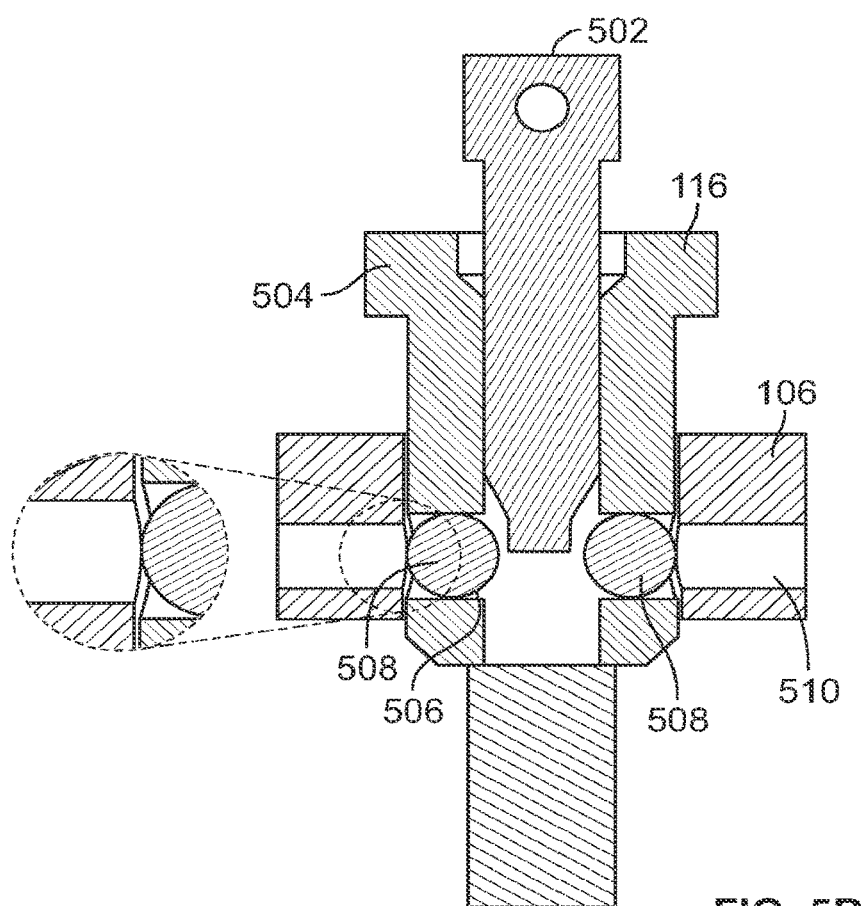
Figure 5C:
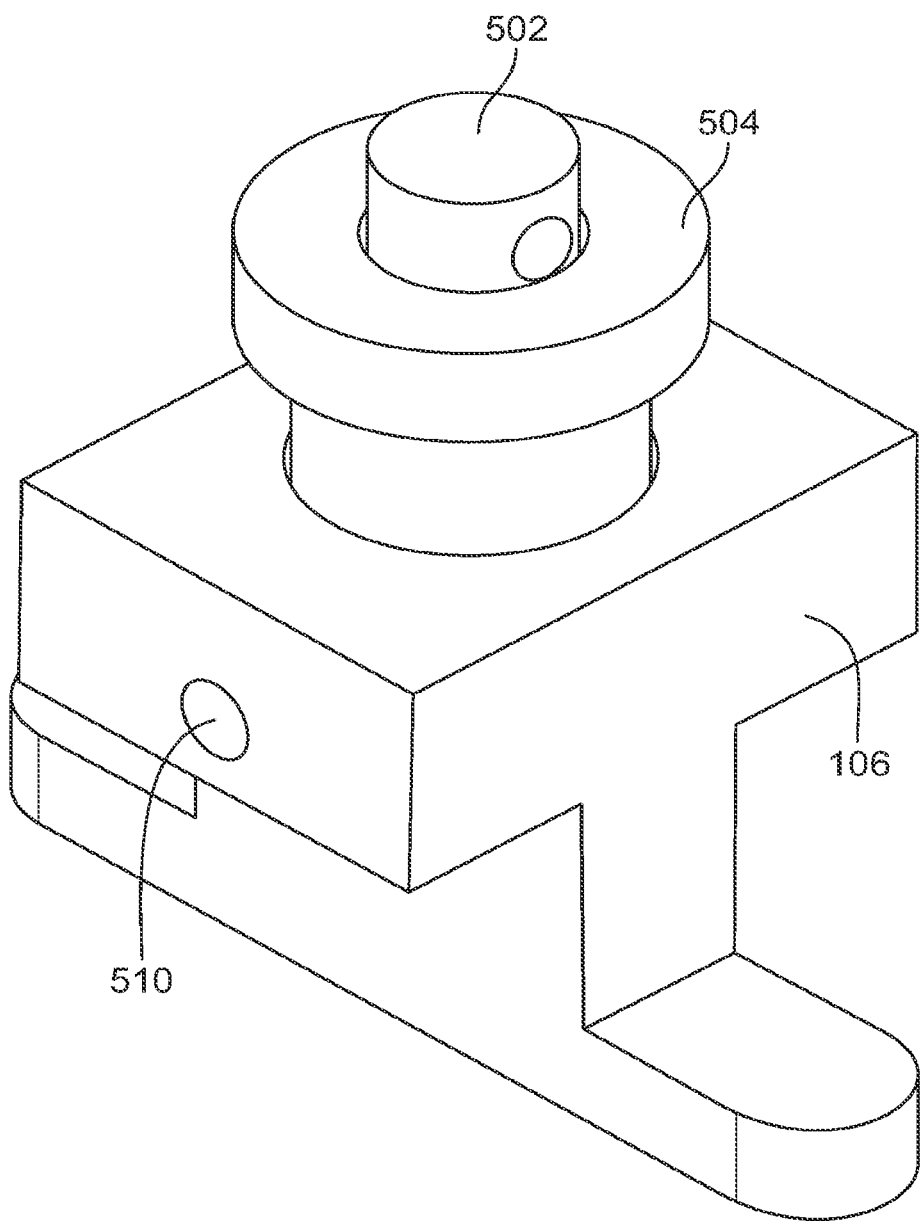

FIGS. 5a and 5b illustrate an exemplary embodiment of the second activator 116. The second activator 116 comprises a pin 502 and a tube 504. The tube 504 includes one or more cross-holes 506. Inside each cross-hole 506 sits a ball 508. The size of the ball 508 is larger than the thickness of the wall of the tube 504. The second activator 116 is situated inside a T-shaped plunger 106 shown in FIG. 5c. The plunger 106 also comprises cross-holes 510 that can be aligned with the cross-holes 506 of the tube 504. When the pin 502 is fully inserted inside the tube 504, it pushes the balls 508 outward partially into the cross-holes 510 of the plunger 106. When the pin 502 is pulled up as shown in FIG. 5b, under the pressure from the plunger 106, the balls 508 are pushed towards the inner side of the tube 504. When the balls 508 roll outside of the cross-holes 510 into the cross-holes 506, the plunger 106 is unblocked to move downward under the force of the compressed springs of the second set 110. As the plunger 106 moves downward, the stored substance, which may be medicinal or non-medicinal, is injected into the injection site through the needle 102. FIG. 3 illustrates the configuration of the auto-injection device 100 after use. The chamber 105 is empty. The first set 108 and the second set 110 of the springs are relaxed.

As shown in FIGS. 1-3, the pin 502 of the second activator 116 is tied to two lugs (708 in FIG. 7 and FIG. 10a) using a string or wire 130. When the syringe 104 begins to move downward under the pressure from the first set of springs 108, the pin 502 is pulled up by the string or wire 130, activating the second set of springs 110.

Figure 6:
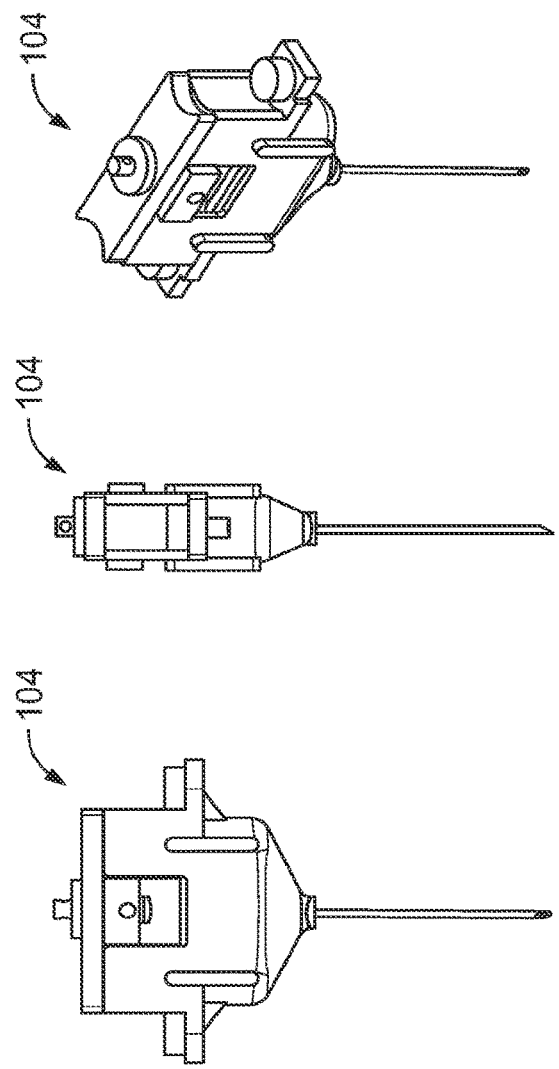
FIG. 6 illustrates different views of an exemplary syringe.
Figure 6:
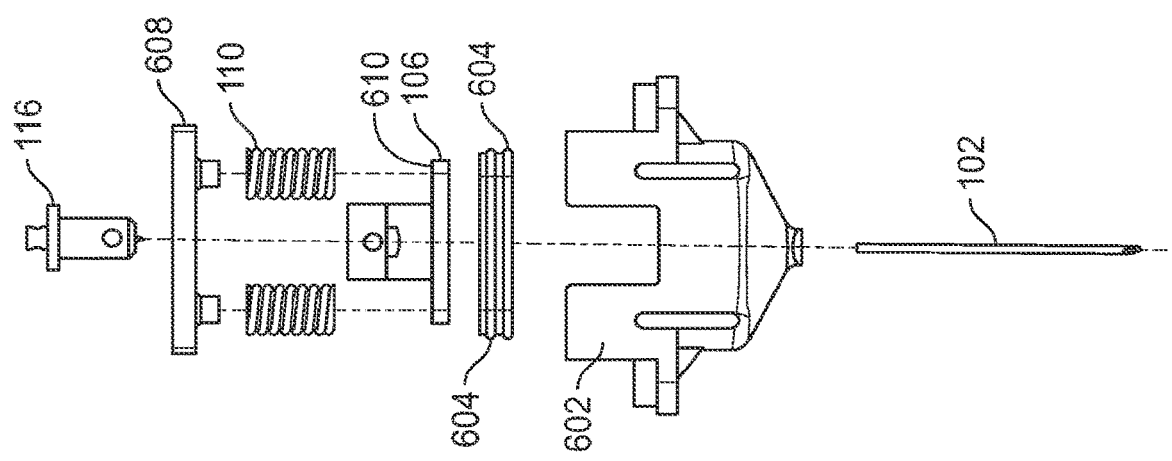

FIG. 6 illustrates different views of the syringe 104. In the exploded view, the different parts of the syringe 104 are depicted. At the top is the second activator 116, which is placed onto the plunger 106 through a syringe cap 608. The syringe cap 608 is configured with a hole at the center for receiving the second activator 106 and two protrusions at the bottom to plug into one end of the springs in the second set 110. The other end of the springs in the second set 110 rests on the flange 610 of the plunger 106. A ribbed plunger plate 604 made of rubber or plastic beneath the plunger 106 seals the chamber 105. The second activator 116, the syringe cap 608, the second set of springs 110, the plunger 106, the plunger plate 604, and the needle 102 are then assembled into the syringe shell 602. The front view, a side view, and a perspective view of the assembled syringe 104 are depicted in FIG. 6 as well.

The assembled syringe 104 and the first set of springs 108 can then be assembled into the casing 120. FIGS. 7-11 illustrate the casing system. FIG. 12 illustrates different views of the assembled auto-injection device 100.

Figure 7:
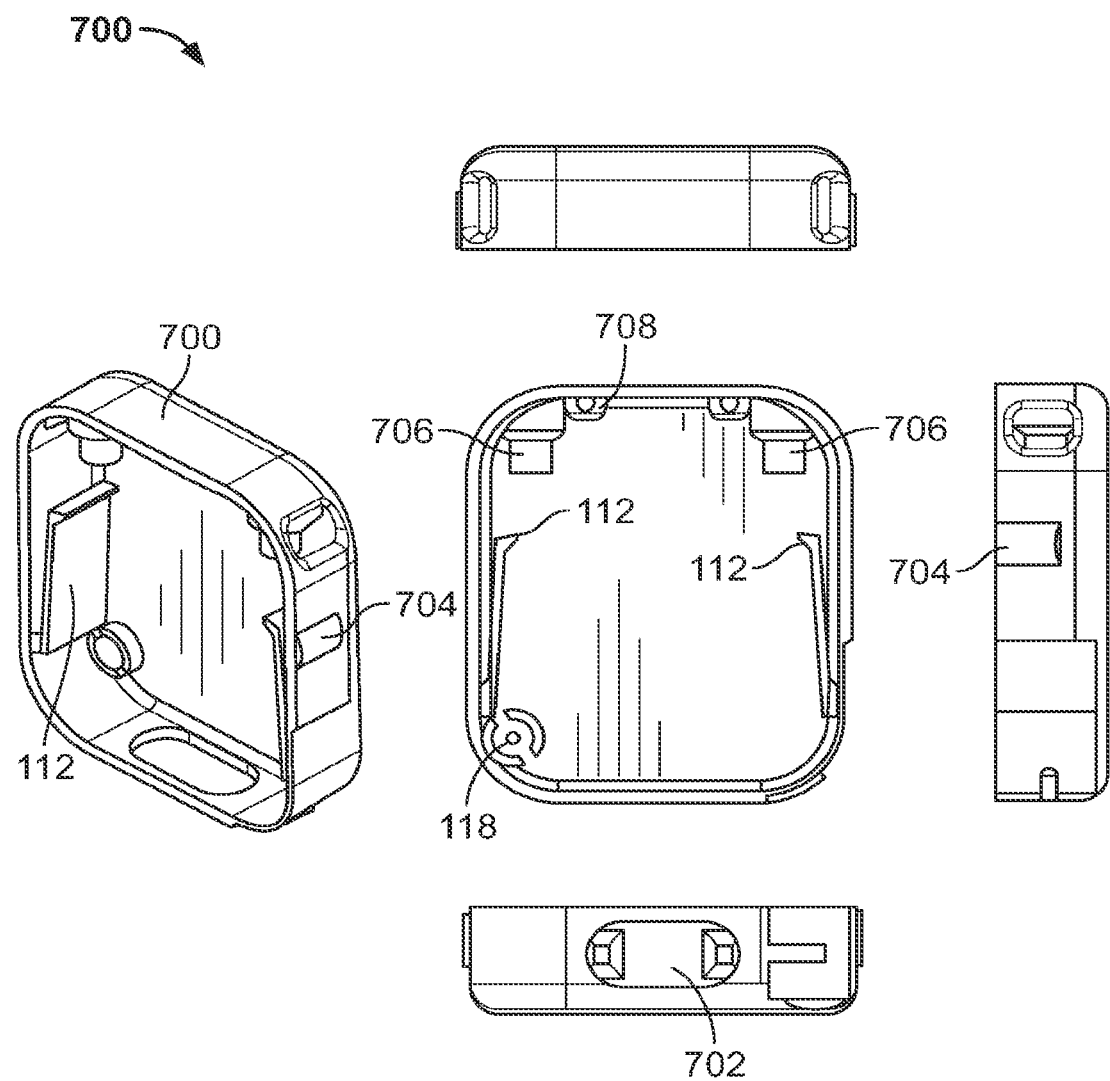
FIG. 7 illustrates an exemplary design of the frame.

FIG. 7 shows the frame 700 of an exemplary casing 120. Different views of the frame 700 are depicted to show different parts. In both the perspective view and the front view, the cantilevers 112 are shown as being affixed to two opposing interior sides of the frame 700. The bottom view shows a hole 702, configured to receive the first activator 114. The side view shows a bump 704 on the outer side of the frame 700 (with another bump on the hidden side not shown). The bumps 704 function to align the frame 700 with matching depressions on the internal side of the outer-cover 1202 (see FIG. 12, depressions not shown). This ensures that the frame 700 (with the auto-injection device 100 inset in it) does not slip off the outer-cover 1202 easily. Some force is required to remove the frame 700 from the outer-cover 1202 by unseating the bumps 704 from the depressions. The front view also shows two stubs or protrusions 706 for holding the first set of springs 108 (see FIG. 12), and two lugs 708 for tying the string or wire 130 that is used to suspend the second activator 116.

Figure 8:
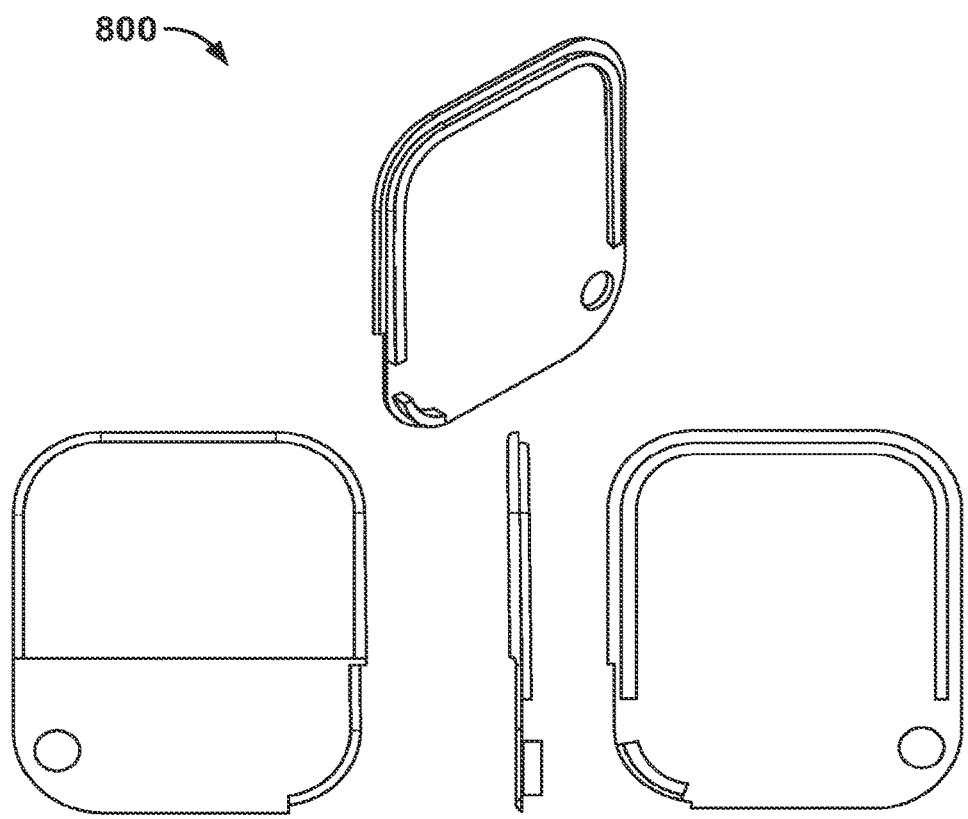
FIG. 8 illustrates an exemplary design of the cover.

FIG. 8 illustrates the perspective view, front and back view, and a side view of a cover 800 for the frame 700. In some embodiments, the cover 800 can be placed on top of the frame 700 to seal the casing 120.

Figure 9:
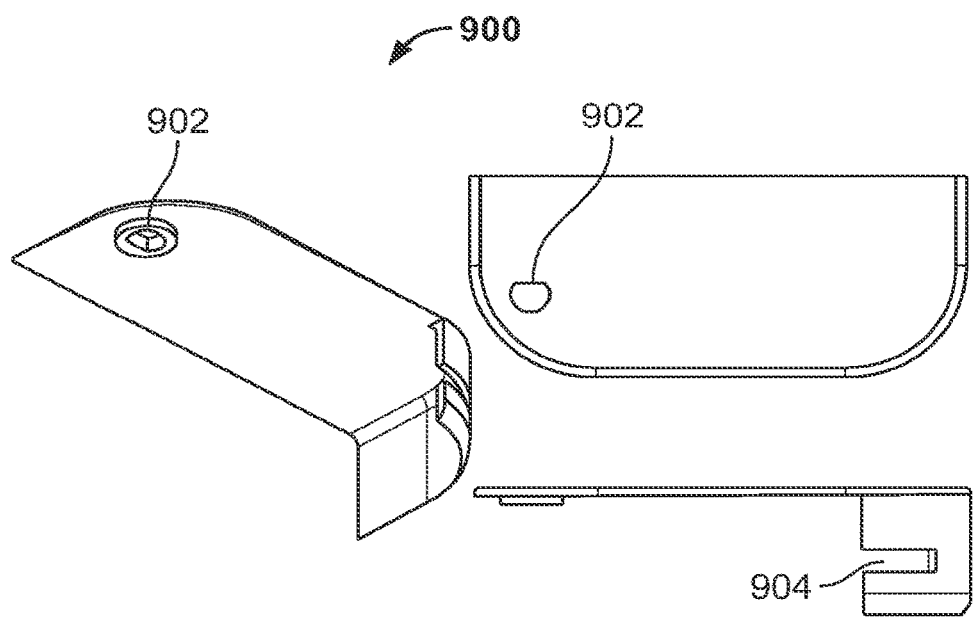
FIG. 9 illustrates an exemplary design of the revolving sheath.

FIG. 9 illustrates a post-injection safety feature that can be installed on the cover 800. The safety feature is a revolving sheath 900. The perspective (left image), front (top-right image) and bottom view (bottom-right image) of the revolving sheath 900 are depicted in FIG. 9. The revolving sheath 900 can be attached to the cover 800 via the aperture 902 and can be open or closed. When in the closed position, the revolving sheath 900 rests on the cover 800 to which it is attached. The revolving sheath 900 can be swirled open after the auto-injection device 100 has been used for injection. In the open position, the revolving sheath 900 covers the needle 102 for safety protection. The slot 904 on the side wall of the revolving sheath 900 accommodates the needle 102. A lock mechanism (shown in FIGS. 10a and 10b) locks the revolving sheath 900 in the open position so that the used needle 102 remains covered.

Figure 10A:
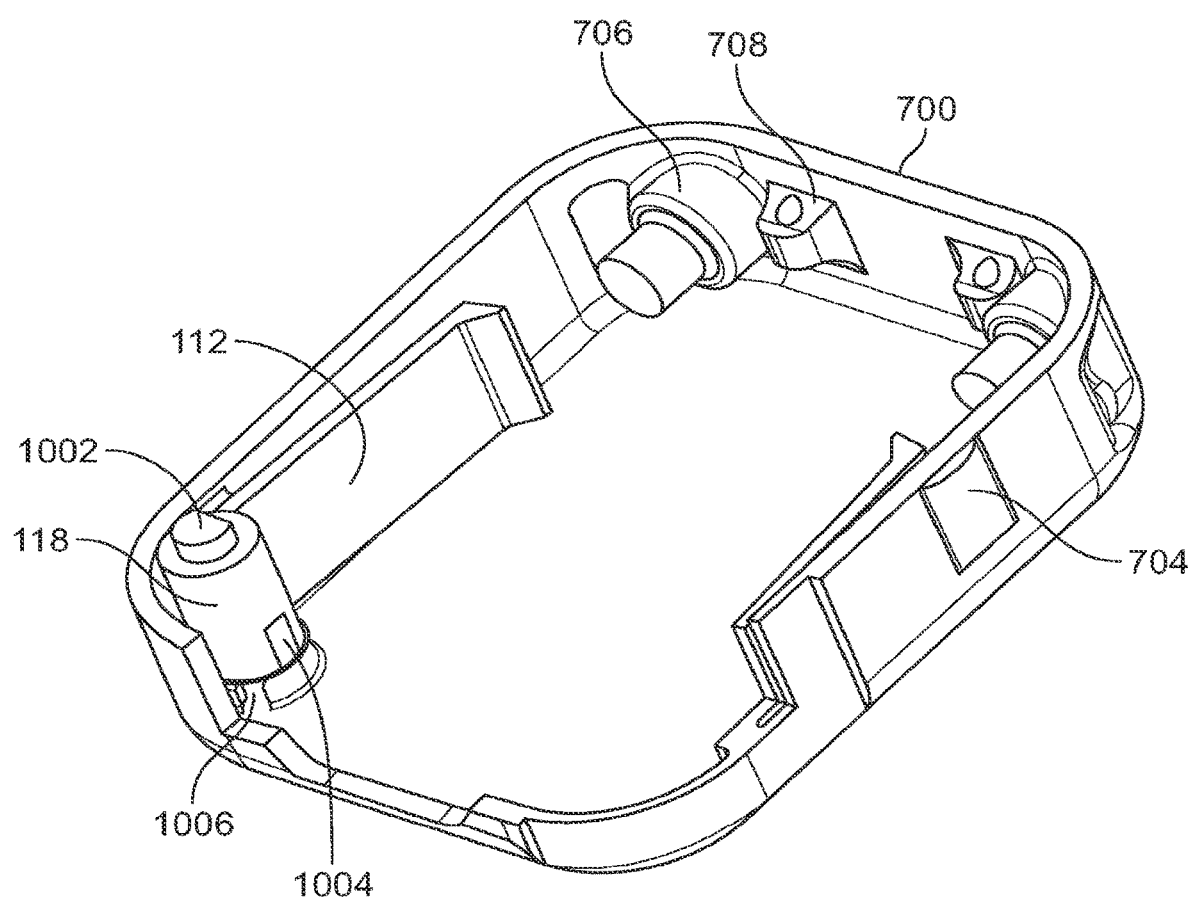
FIGS. 10a-10b illustrate an exemplary design of the revolving peg as a safety feature.
Figure 10B:
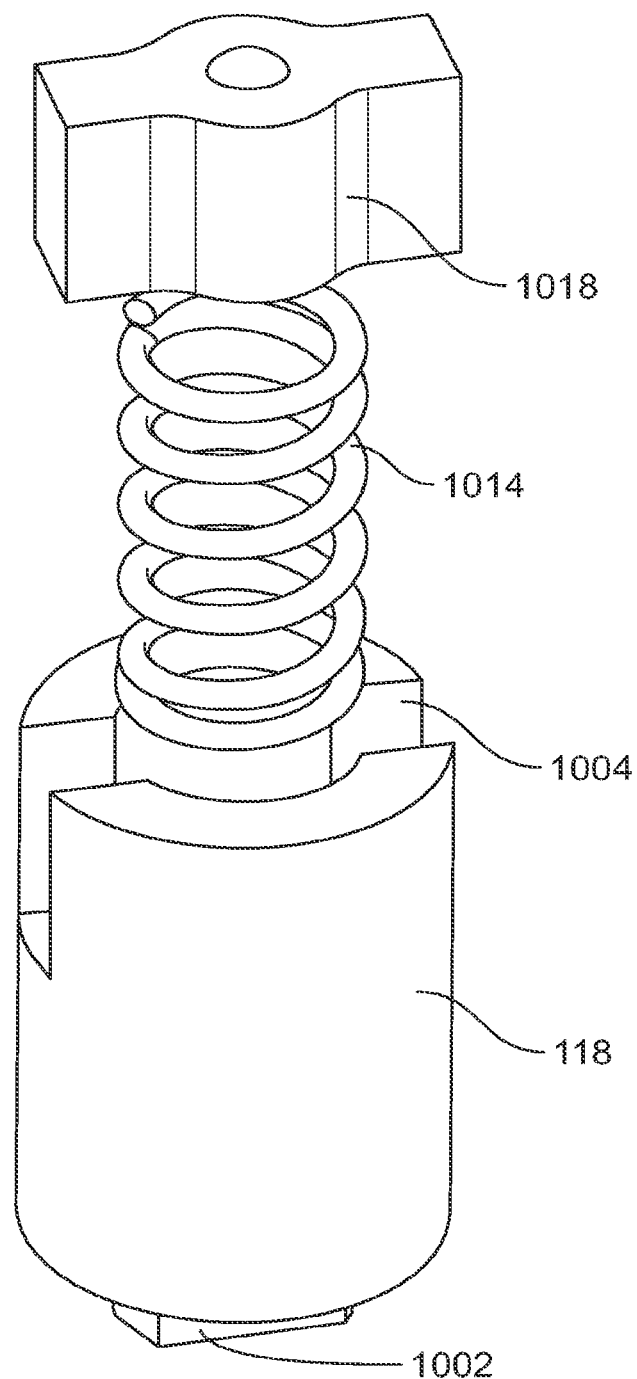

In one embodiment, the revolving sheath 900 is attached to the frame 700 via a revolving peg 118 illustrated in FIGS. 10a-10b. As shown in FIG. 10a, the revolving peg 118 is the cylindrical peg located in the lower left corner of the frame 700. The revolving peg 118 comprises a D-shaped button 1002 at the top that matches the shape of the aperture 902 on the sheath 900 and allows the revolving sheath 900 to be attached. The revolving peg 118 further comprises a slot 1004, which can be aligned with the slot 1006 located at the base of the revolving peg 118 through rotation. When the revolving sheath 900 is pushed open, the revolving peg 118 is turned by the coupling force via the D-shaped button 1002. The revolving peg 118 includes a spring 1014 and a revolving key 1018, as shown in FIG. 10b. The revolving key 1018 can be fitted into the slot 1004 when the spring 1014 is compressed. The revolving peg 118 rotates with the revolving sheath 900, which also rotates the revolving key 1018 as the key 1018 is fitted inside the slot 1004. Once the two slots 1004 and 1006 become aligned, the spring 1014 pushes the key 1018 down so that the key 1018 engages the slot 1006. Because the height of the key 1018 is greater than that of the slot 1006, the key 1018 sits fully within the slot 1006 and partially within the slot 1004. This prevents relative rotation between the slot 1006 and the revolving peg 118, thus locking the revolving sheath 900 in front of the needle 102.

Figure 11:
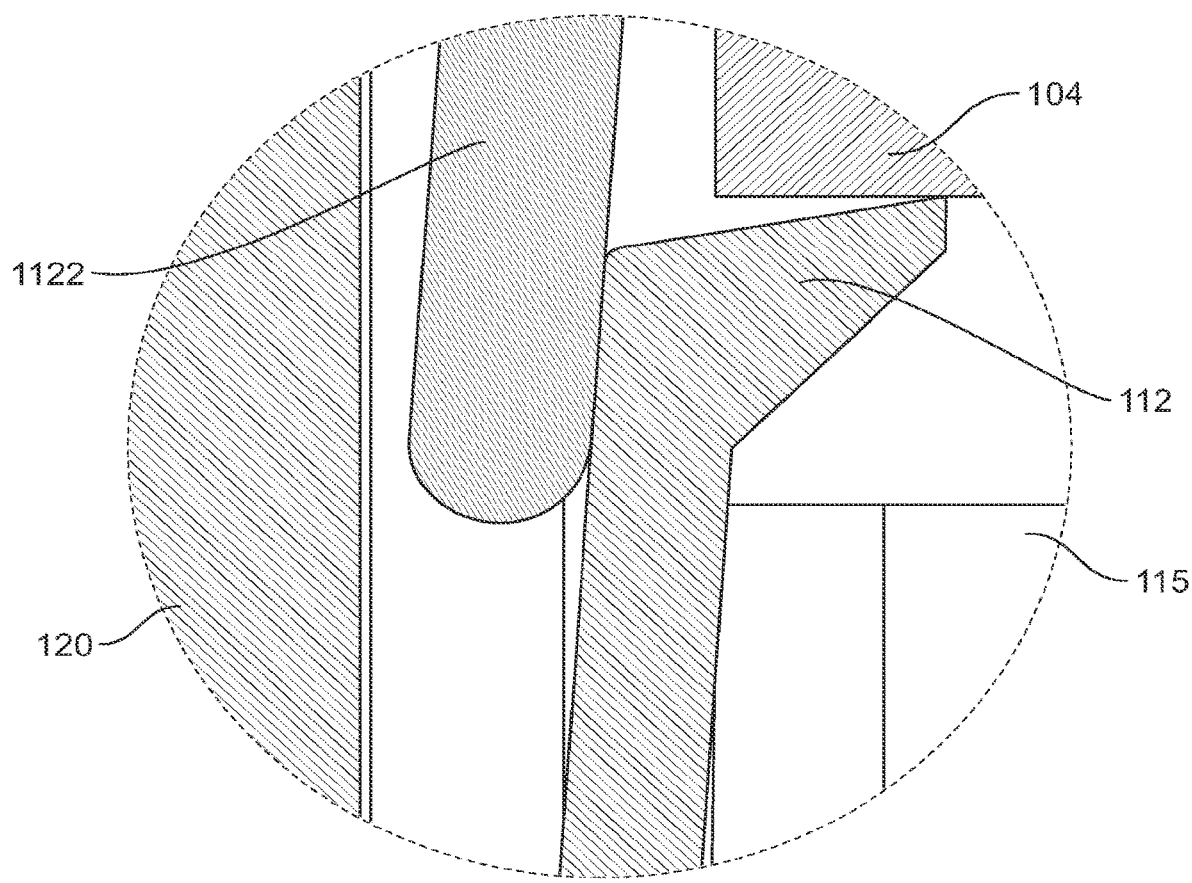
FIG. 11 illustrates an exemplary design of a flap as another safety feature.
Figure 12:
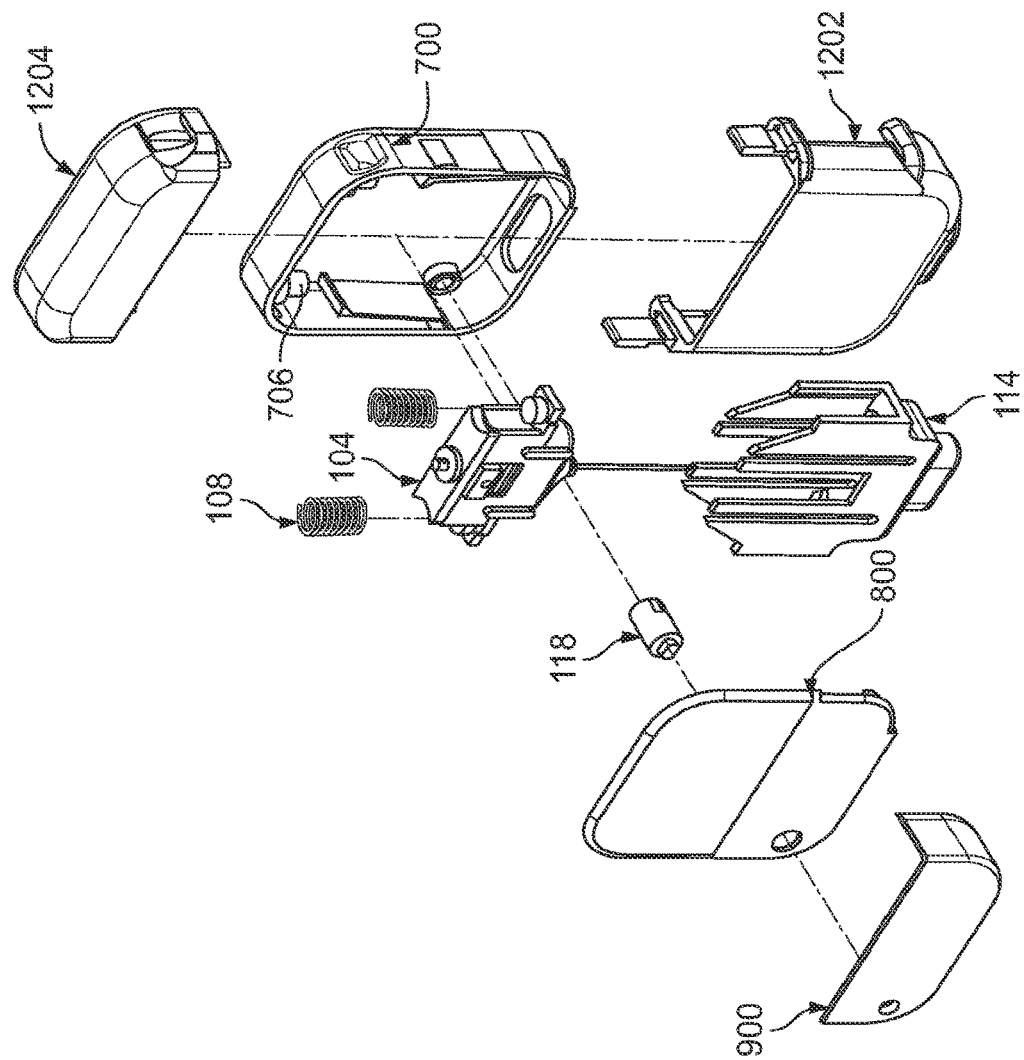
FIG. 12 illustrates different views of an assembled auto-injection device.
Figure 12:
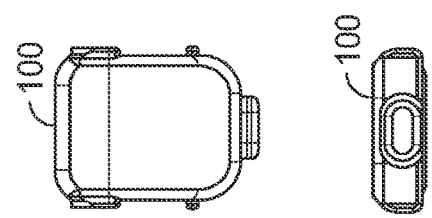
Figure 12:
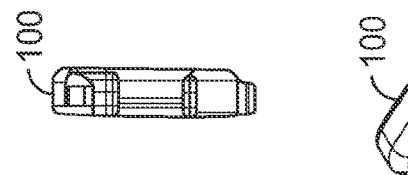
Figure 12:
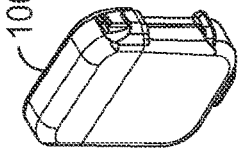

FIG. 11 illustrates another safety feature. In FIG. 11, the cantilevers 112 (only one is shown) stand against a flap 1122 of the outer-cover (1204 or 1202 shown in FIG. 12). When the auto-injection device 100 is stowed inside the outer-cover 1204 and 1202, the flaps 1122 jam the first activator 114 and prevents the first activator 114 from bending the cantilever 112. This safety feature ensures that the auto-injection device 100 will not activate until it is taken out of the outer-covers 1204 and 1202.

FIG. 12 shows different views of an assembled auto-injection device 100. On the left are four views of the assembled auto-injection device 100 enclosed in the outer-covers. Starting from the top left and going clockwise, the views are a side view, the front view, the bottom view, and a perspective view of the enclosed device 100. On the right is an exploded view of the assembled auto-injection device 100. The first set of springs 108, the syringe 104, and the first activator 114 are assembled into the syringe shell (602, not labeled) before being fitted into the frame 700, with the two stubs 706 of the frame 700 being inserted into the springs 108 and a string or wire 130 tying the second activator 116 to the lugs of the frame 700 (not shown). The revolving sheath 900, the cover 800, and the revolving peg 118 (along with the revolving key 1018 and the revolving spring 1014) are then assembled onto the frame 700. The two outer-covers 1202 and 1204 are protective covers. As illustrated in FIG. 11, one or both of the two outer-covers 1202 and 1204 may include one or more flaps 1122. When the auto-injection device 100 is stowed inside the outer-covers, the flaps 1122 are pressed against the cantilevers 112, preventing the cantilevers 112 from bending or moving outwardly so that the syringe 104 does not fall off the cantilevers 112 by accident.

Figure 13:
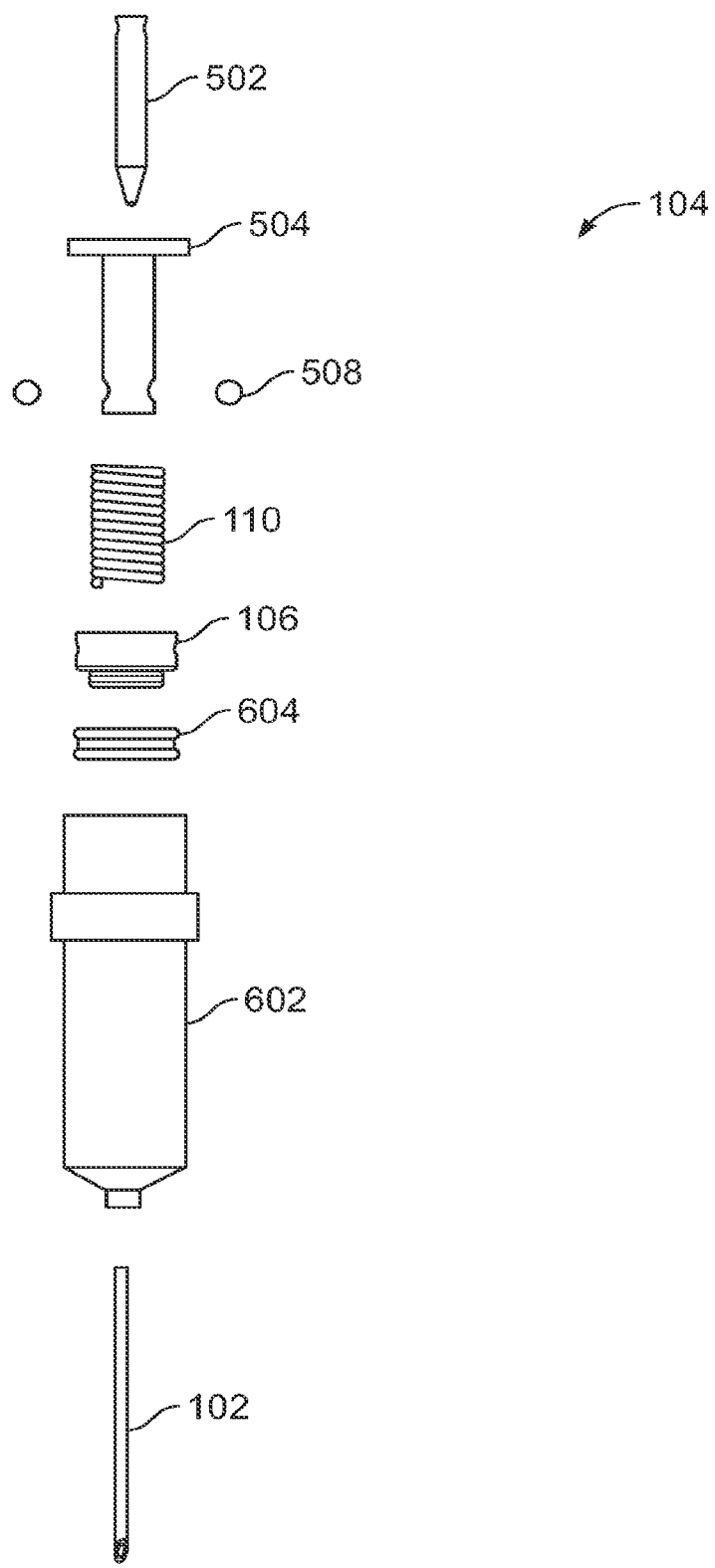
FIG. 13 illustrates an exploded view of a second exemplary embodiment of the syringe in an auto-injection device.
Figure 14:
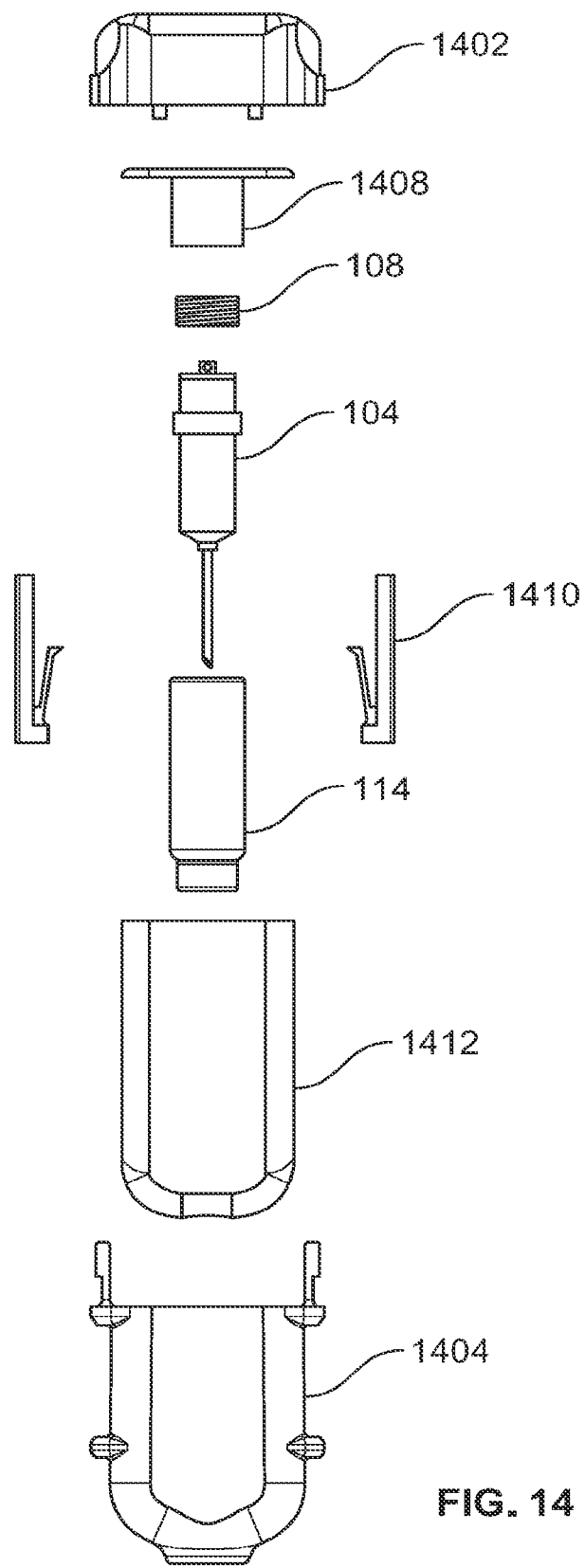
FIG. 14 illustrates an exploded view of a second exemplary embodiment of the assembled auto-injection device.

FIG. 13 and FIG. 14 illustrate a second embodiment of the syringe 104. Instead of using sets of two springs, the embodiment in FIGS. 13 and 14 uses one spring for each set. In FIG. 13, the pin 502 is inserted into the tube 504. Along with the two identical balls 508, they form the second activator 116, which is placed onto the second spring 110, installed on top of the plunger 106 along with the plunger plate 604, and inserted into the syringe shell 602 that also accommodates the needle 102. After the syringe 104 is assembled, it is then placed into a frame 1410, a cover 1412, and out-covers 1402 and 1404 to produce an assembled auto-injection device 100 as shown in FIG. 14.

FIG. 14 depicts an exploded view of the second embodiment of the auto-injection device 100. In FIG. 14, the assembled syringe 104 (shown in FIG. 13) is inserted into a first activator 114, along with a first spring 108 and a cap 1408. The assembled system is then encased by different parts of the casing 120, e.g., 1410 and 1412. The encased auto-injection device 100 are covered by a top outer-cover piece 1402 and a bottom out-cover piece 1404. Similar to the out-covers shown in FIG. 12, the out-covers 1402 and 1404 can jam the first activator 114 and prevent the auto-injection device 100 from being activated when it is stowed inside the out-covers.

It is noted that the frame 1410, shown in FIG. 14 as comprising two separate pieces, can in fact comprise one or multiple pieces. For instance, the frame 1410 may be an annular ring and the cantilevers 112 is a one-piece component within the annular ring. For another instance, the frame 1410 may comprise two or more arcs that can be made into one annular ring and each arc of the frame 1410 includes a cantilever structure 112.

FIGS. 15a-15d illustrate a third embodiment of the auto-injection device 100. In this embodiment, the auto-injection device 100 has a casing 120 (e.g., frame 700 and cover 800) that changes shape by extending along the axis of the needle 102 using a telescoping mechanism. In this embodiment, the casing comprises three separate components that together enclose the internal mechanisms. The set of activation spring(s) 108 begin compressed and pushes the rear section of the casing 120 away from the tip of the needle 102 once the outer cover 1402 is removed. Attached to the rear section of the casing 120 are small snap-fit pieces that move parallel to the body of the device 100 within a confined space. The confined space compresses the snap-fit pieces such that they begin in a compressed state.

When the rear section of the casing 120 reaches the end of its moving path, the snap-fit pieces (1502 in FIGS. 15a-15d) exit the confined space and are allowed to expand. In their expanded state, the snap-fit pieces cannot return to the confined space, so the rear section of the casing 120 cannot be pushed back towards the tip of the needle 102. After the body has expanded, the set of activation springs 108 remain in a partially compressed state. This ensures that they can push the needle 102 out of the device 100 upon activation.

Figure 15A:
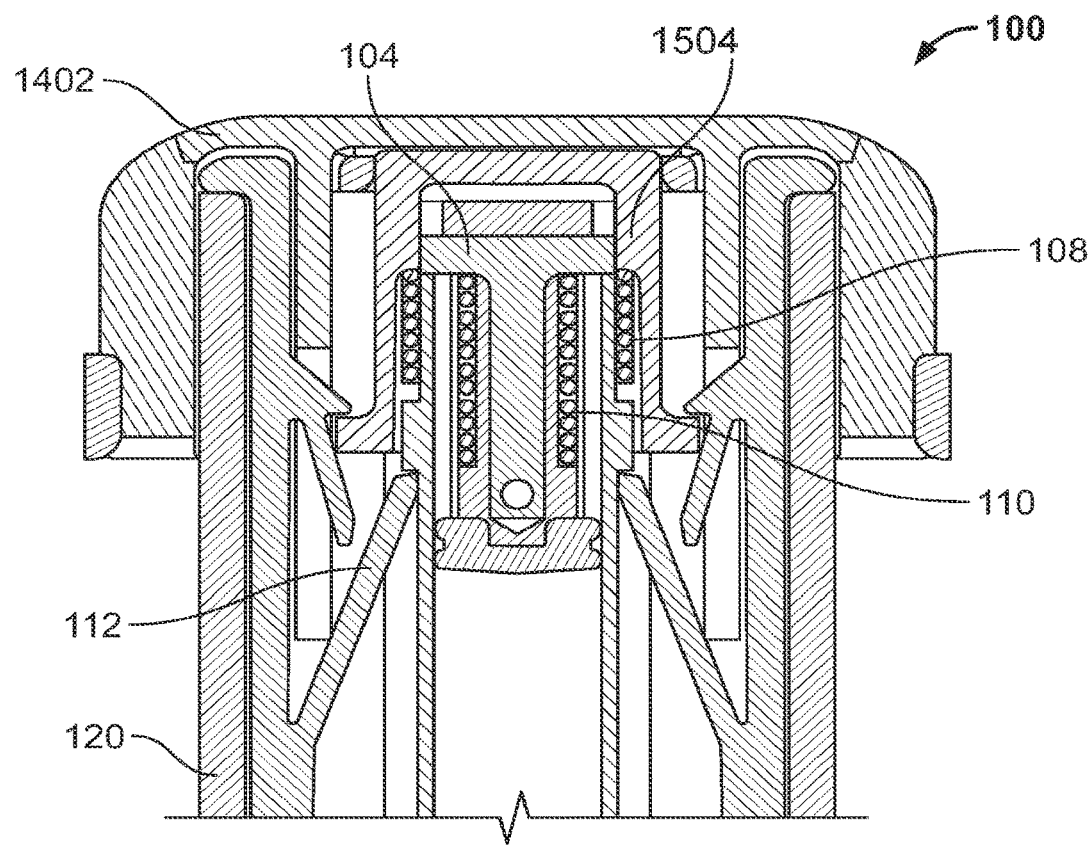
FIGS. 15a-15d illustrates a third exemplary embodiment of the auto-injection device.
Figure 15B:
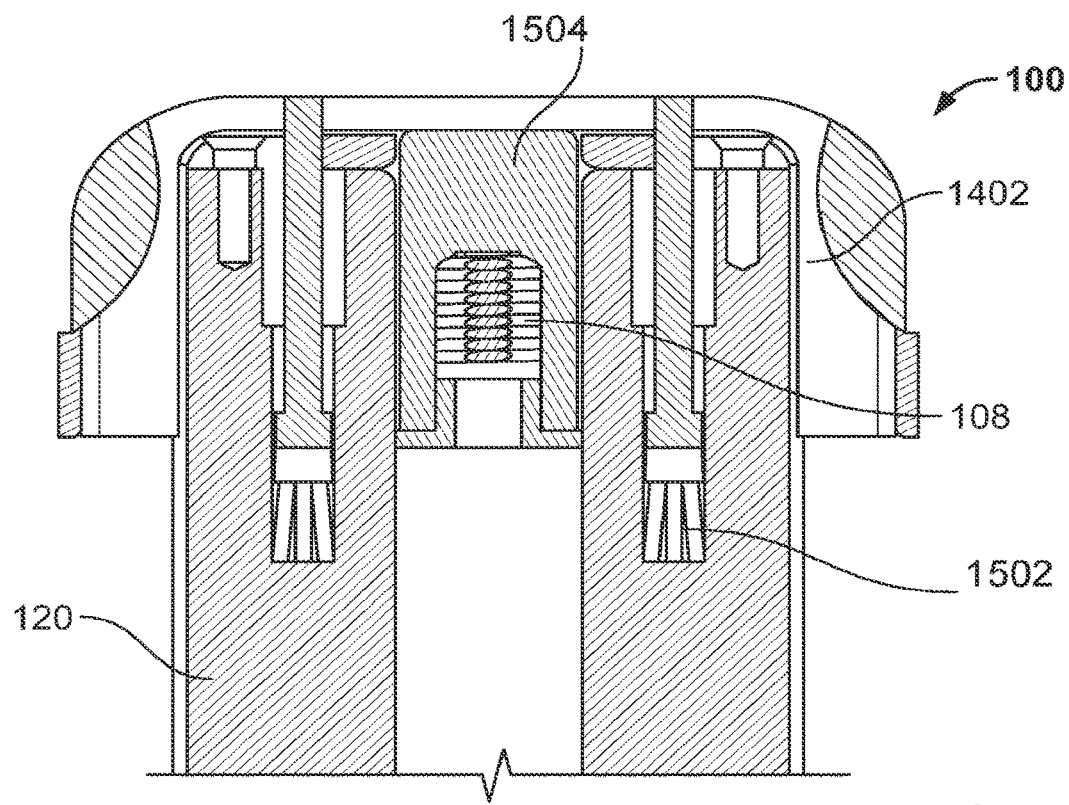

FIGS. 15a-15b show the mid-plane views of the auto-injection device 100 in a compressed state. FIG. 15a is a mid-plane view of the springs 108 being compressed. FIG. 15b is a mid-plane view of the snap-fit pieces in a compressed position.

Figure 15C:
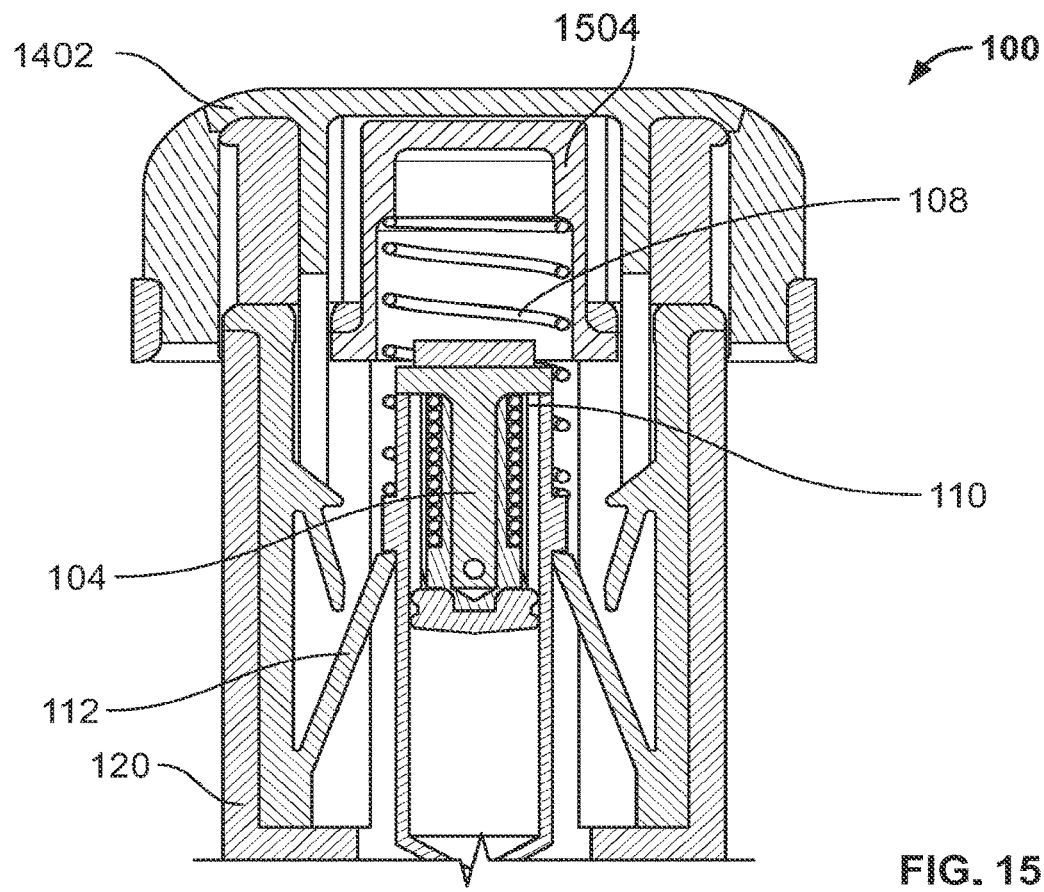
Figure 15D:
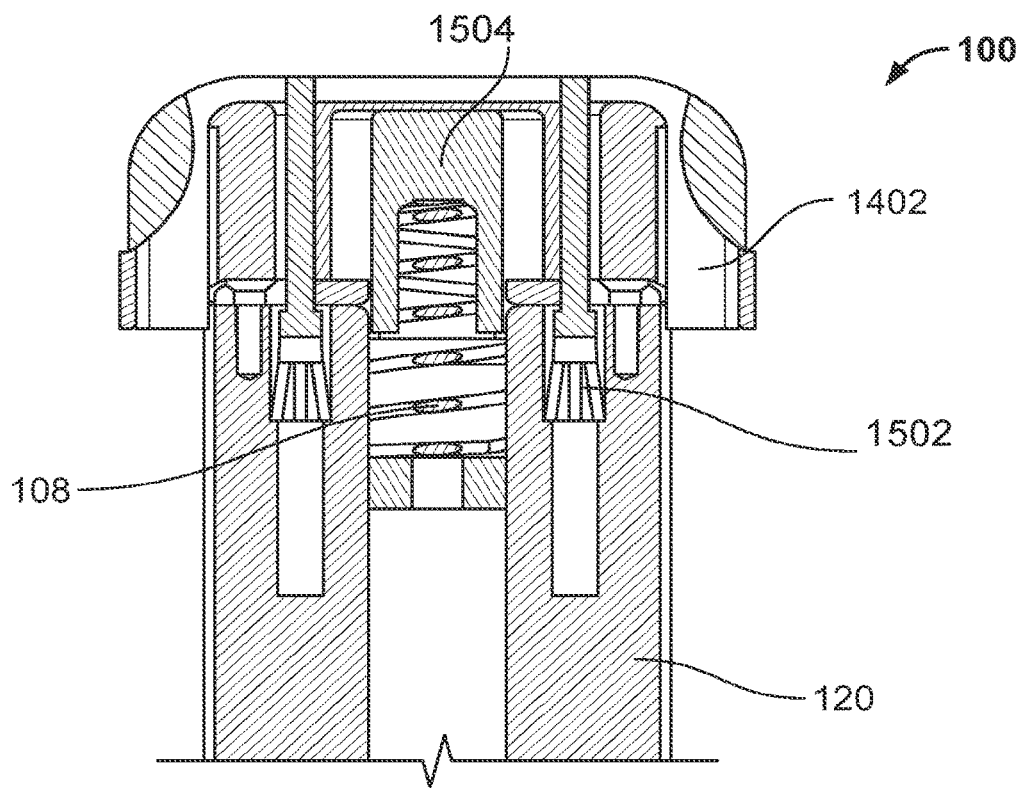

FIGS. 15c-15d show the mid-plane views of the auto-injection device 100 in an extended state. FIG. 15c is a mid-plane view of the springs 108 that has partially expanded. FIG. 15d is a mid-plane view of the snap-fit pieces. In FIG. 15d, the snap-fit pieces 1502 are in an extended position that prevents them from moving back. A cap 1504 of the case moves outwards to complete the telescoping action.

Figure 16:
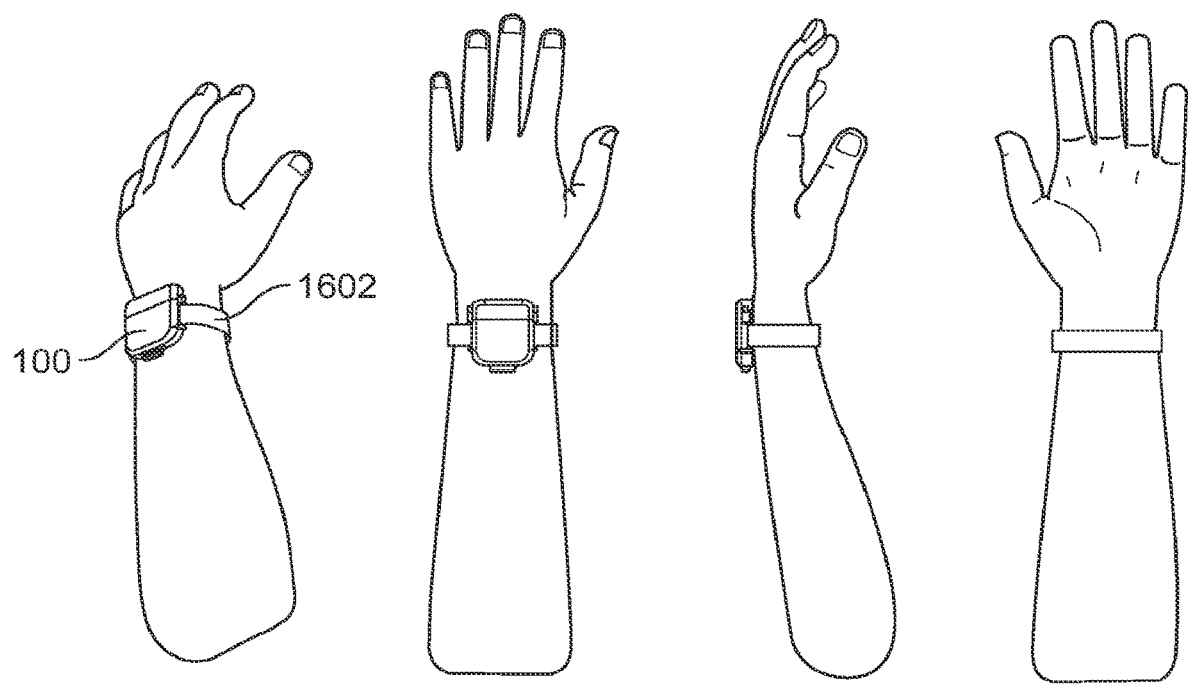
FIG. 16 illustrates an exemplary wearable device comprising the auto-injection device.

FIG. 16 illustrates an embodiment of a wearable auto-injection device 100. In some embodiments, the assembled auto-injection device 100 is light and compact and made in the shape of a watch. The out-covers (1202 and 1204 in FIGS. 12 and 1402 and 1404 in FIG. 14) are fitted with lugs to accommodate straps 1602 so that the auto-injection device 100 can be worn like a watch. The wrist-mounted device 100 in FIG. 16 can be carried by a patient for emergency use. In other embodiments, the out-covers can be made to resemble a piece of jewelry or toy.

The auto-injection devices 100 disclosed herein have many applications, medical or non-medical. The size of the chamber 105 in the auto-injection device 100 can be manufactured in accordance with the requirement of each application. In some applications, the size of the chamber 105 can be made fairly standard. In other applications, the size of the chamber 105 may be personalized. As mentioned in the background section, the auto-injection device 100 is useful in anaphylaxis and hyperglycemia emergency situations. The auto-injection device 100 can be useful in opioid overdose emergencies as well. Indeed, in many life-threatening situations, auto-injection devices disclosed herein can save lives by providing timely relief of the symptoms.

Although the disclosure is illustrated and described herein with reference to specific embodiments, the disclosure is not intended to be limited to the details shown. Rather, various modifications may be made in the details within the scope and range of equivalents of the claims and without departing from the disclosure.

The invention claimed is:

1. A pharmaceutical injection assembly comprising:
   a casing having a band carried thereby for being worn by a user and for storing the injection assembly;
   an injection device initially carried within the casing, the injection device being removable from the casing by displacement of a cap on the casing;
   wherein the injection device comprises:
      a housing;
      a first activator having a protrusion extending outwardly from a first end of the housing, the first activator being biased to extend the protrusion outwardly relative to the housing, the protrusion defining a contact surface for being pressed against an injection site of the user;
      a syringe within the housing and having a needle extending forward towards an aperture defined in the protrusion, wherein, in operation, the syringe is translated towards the first end of the housing when the first activator is translated towards the syringe;
      a first spring providing a spring force that biases the syringe towards the first end of the housing; and a detent extending rearward within the housing, the detent having a forward end affixed to an interior side of the housing and a rearward end opposite the forward end, wherein the rearward end of the detent, when in a first position thereof, supports the syringe against the spring force of the first spring;

wherein movement of the protrusion inwardly relative to the housing translates the first activator towards the syringe and imparts movement of the rearward end of the detent laterally away from the syringe thereby releasing the syringe to be moved towards the first end of the housing under the spring force of the first spring, wherein the syringe further comprises:
 a plunger;
 a forward end from which the needle extends;
 a chamber for storing an injection substance between the plunger and forward end of the syringe; and
 a second activator, wherein, when the syringe is released, forward movement of the syringe towards the first end of the housing causes activation of the second activator and movement of the plunger towards the forward end of the syringe to dispense the injection substance through the needle for injection into the user, wherein the second activator begins to move forward along with the plunger when the syringe is released, wherein the second activator comprises a pin that begins to move forward with the plunger when the syringe is released, and wherein the pin, after beginning to move forward with the plunger when the syringe is released, is pulled thereby activating the second activator.

2. The assembly of claim 1, wherein the first spring biases the syringe outwardly to cause the needle to extend outwardly through the aperture when the first activator imparts movement of the rearward end of the detent laterally away from the syringe thereby releasing the syringe.

3. The assembly of claim 1, wherein the syringe comprises a second spring that begins to move forward with the plunger when the syringe is released.

4. The assembly of claim 3, wherein the second spring is initially compressed until movement of the syringe towards the first end of the housing causes activation of the second activator.

5. The assembly of claim 1, wherein the first spring is initially compressed until movement of the detent is imparted.

6. The assembly of claim 1, wherein the housing is configured to extend or retract via a telescoping mechanism to accommodate the assembly.

7. The assembly of claim 1, wherein the casing includes one or more protrusions to jam the detent when the device is stowed in the casing, to prevent the device from being activated accidentally.

8. The assembly of claim 1, wherein the housing includes a needle cover that can be rotated to shroud the needle once the needle has translated outwardly of the housing.

9. The assembly of claim 1, wherein the pin is pulled by an element attached to the housing, thereby activating the second activator, after the pin has moved forward with the plunger a predetermined distance.

10. The assembly of claim 1, wherein the second activator comprises a movable element maintained in engagement with the plunger by the pin until the pin is pulled.

11. The assembly of claim 1, wherein the second activator comprises:

at least one ball engaged with the plunger before the syringe is released; and wherein the pin is attached to the housing and maintains the ball in engagement with the plunger before the syringe is released, wherein, when the syringe is released, the pin releases the at least one ball from engagement with the plunger thereby activating the second activator and causing movement of the plunger towards the forward end of the syringe to dispense the injection substance through the needle.

12. The assembly of claim 11, wherein the second activator comprises a set of balls engaged with the plunger before the syringe is released.

13. The assembly of claim 1, wherein the affixed forward end of the detent is closer to the contact surface of the protrusion than the rearward end of the detent is to the contact surface of the protrusion.

14. A pharmaceutical injection assembly comprising: a casing having a band carried thereby for being worn by a user and for storing the injection assembly; an injection device initially carried within the casing, the injection device being removable from the casing by displacement of a cap on the casing; wherein the injection device comprises: a housing; a first activator having a protrusion extending outwardly from a first end of the housing, the first activator being biased to extend the protrusion outwardly relative to the housing, the protrusion defining a contact surface for being pressed against an injection site of the user; a syringe within the housing and having a needle extending forward towards an aperture defined in the protrusion, wherein, in operation, the syringe is translated towards the first end of the housing when the first activator is translated towards the syringe; a first spring providing a spring force that biases the syringe towards the first end of the housing; and a detent extending rearward within the housing, the detent having a forward end affixed to an interior side of the housing and a rearward end opposite the forward end, wherein the rearward end of the detent, when in a first position thereof, supports the syringe against the spring force of the first spring; wherein movement of the protrusion inwardly relative to the housing translates the first activator towards the syringe and imparts movement of the rearward end of the detent laterally away from the syringe thereby releasing the syringe to be moved towards the first end of the housing under the spring force of the first spring, wherein the syringe further comprises: a plunger; a forward end from which the needle extends; a chamber for storing an injection substance between the plunger and forward end of the syringe; and a second activator, wherein, when the syringe is released, forward movement of the syringe towards the first end of the housing causes activation of the second activator and movement of the plunger towards the forward end of the syringe to dispense the injection substance through the needle for injection into the user, wherein the second activator begins to move forward along with the plunger when the syringe is released, wherein the second activator comprises: at least one ball engaged with the plunger before the syringe is released; and a pin attached to the housing and maintaining the ball in engagement with the plunger before the syringe is released, wherein, when the syringe is released, the pin releases the at least one ball from engagement with the plunger thereby activating the second activator and causing movement of the plunger towards the forward end of the syringe to dispense the injection substance through the needle.

15. The assembly of claim 14, wherein the second activator comprises a set of balls engaged with the plunger before the syringe is released.

\* \* \* \* \*